United States Patent
Bock et al.

(10) Patent No.: US 7,539,363 B2
(45) Date of Patent: May 26, 2009

(54) FIBER OPTIC PROBE FOR DETECTING THE PRESENCE OR ABSENCE OF ONE OR MORE SUBSTANCES WITHIN A MEDIUM

(75) Inventors: Wojtek J. Bock, Ottawa (CA); Jianjun Ma, Gatineau (CA)

(73) Assignee: Universite du Quebec en Outaouais, Gatineau, Quebec (CA)

( * ) Notice: Subject to any disclaimer, the term of this patent is extended or adjusted under 35 U.S.C. 154(b) by 0 days.

(21) Appl. No.: 11/695,479

(22) Filed: Apr. 2, 2007

(65) Prior Publication Data

US 2007/0230859 A1    Oct. 4, 2007

Related U.S. Application Data

(60) Provisional application No. 60/788,797, filed on Apr. 3, 2006.

(51) Int. Cl.
*G02B 6/00* (2006.01)
*G02B 6/255* (2006.01)
*G02B 6/02* (2006.01)

(52) U.S. Cl. .......................... 385/12; 385/96; 385/125

(58) Field of Classification Search ................... 382/12, 382/33, 95–99, 123, 125
See application file for complete search history.

(56) References Cited

U.S. PATENT DOCUMENTS 4,223,226 A    9/1980  Quick
4,652,143 A *  3/1987  Wickersheim et al. ...... 374/161
4,956,558 A *  9/1990  Batishko et al. .......... 250/461.1

FOREIGN PATENT DOCUMENTS

JP    2003-307653    * 10/2003

OTHER PUBLICATIONS

Jianjun Ma and Wojtek J. Bock, "Modeling of photonic crystal fiber with air holes sealed at the fiber end and its application to fluorescent light collection efficiency enhancement", Optics Express, Apr. 4, 2005, vol. 13, No. 7 pp. 2385-2393.

(Continued)

*Primary Examiner*—Charlie Peng
(74) *Attorney, Agent, or Firm*—Shin Hung; Borden Ladner Gervais LLP

(57) ABSTRACT

A fiber optic probe for capable of simultaneously enhancing fluorescent emission collection and reducing stray excitation light noise levels while detecting the presence or absence of one or more substances within a medium. The probe includes an illuminating optical fiber for guiding excitation light from a light source to be launched from an end face of the illuminating optical fiber. A film or an immersion medium emits light when illuminated by the excitation light. The emitted light has a central wavelength that is different than a central wavelength of the excitation light. A receiving optical fiber receives and guides the emitted light. The receiving fiber may be a photonic crystal fiber having an end portion which is a solid segment of glass for improved light collection efficiency. A lens may be provided at the end of the receiving fiber. A detector detects light from the receiving optical fiber.

20 Claims, 13 Drawing Sheets

OTHER PUBLICATIONS

Jianjun Ma and Wojtek J. Bock, "Towards optimum sample-probe-spectrometer system design by adjusting receiving fiber end face position and probe-membrane sample separation", Optics Express, Nov. 14, 2005, vol. 13, No. 23 pp. 9492-9501.

Jianjun Ma and Wojtek J. Bock, "Investigation of large-core photonic crystal fiber sensor for enhancement of fluorescent light collection of polymer membrane", Photonic Applications in Devices and Communication Systems, Proc. of SPIE vol. 5970, pp. 597006-1-597006-6, Oct. 12, 2005.

* cited by examiner

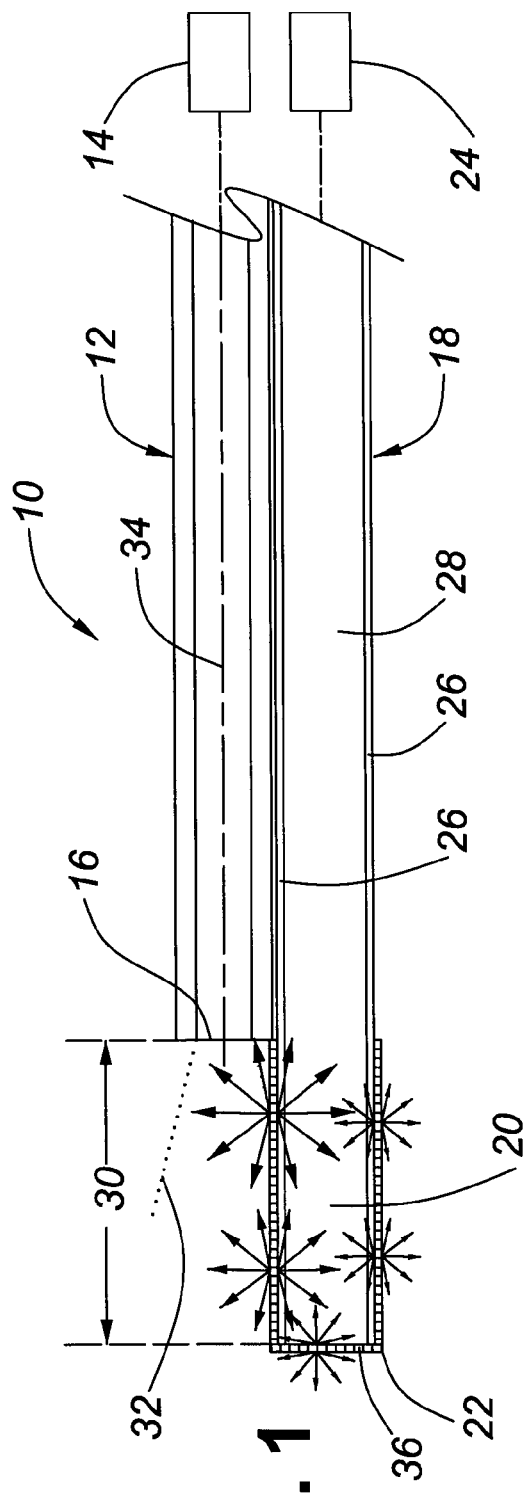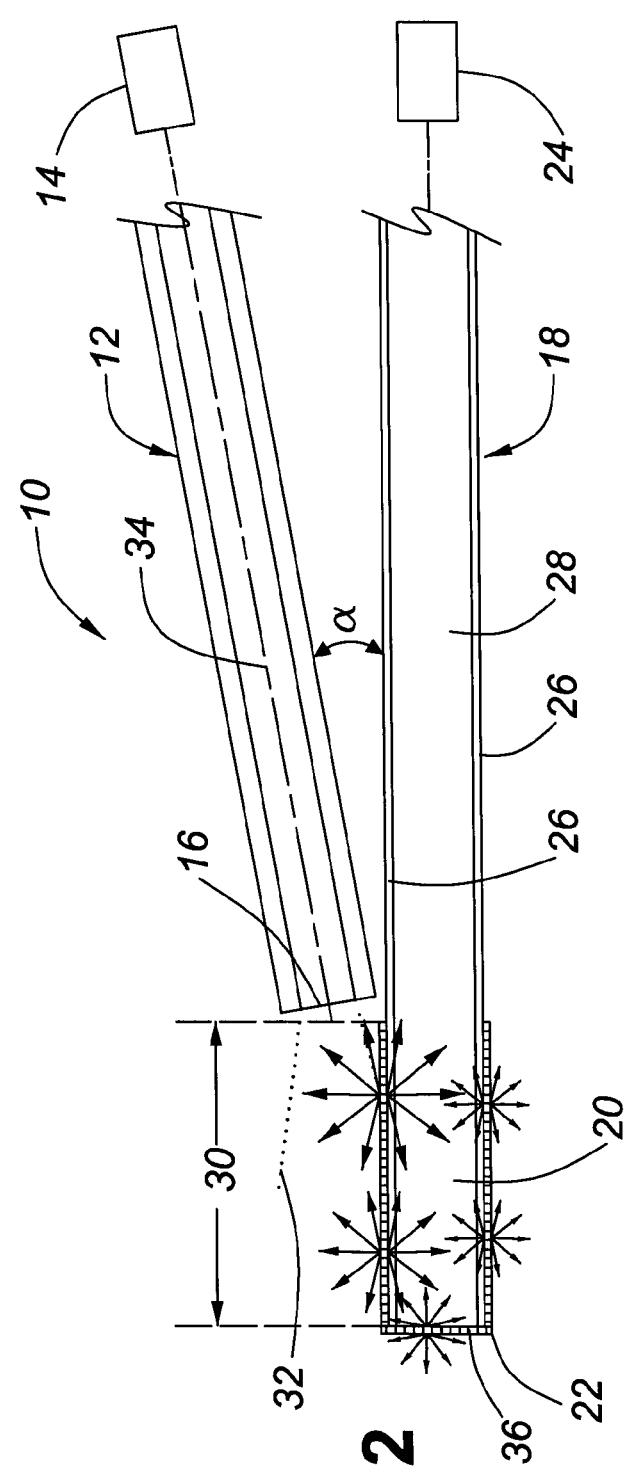

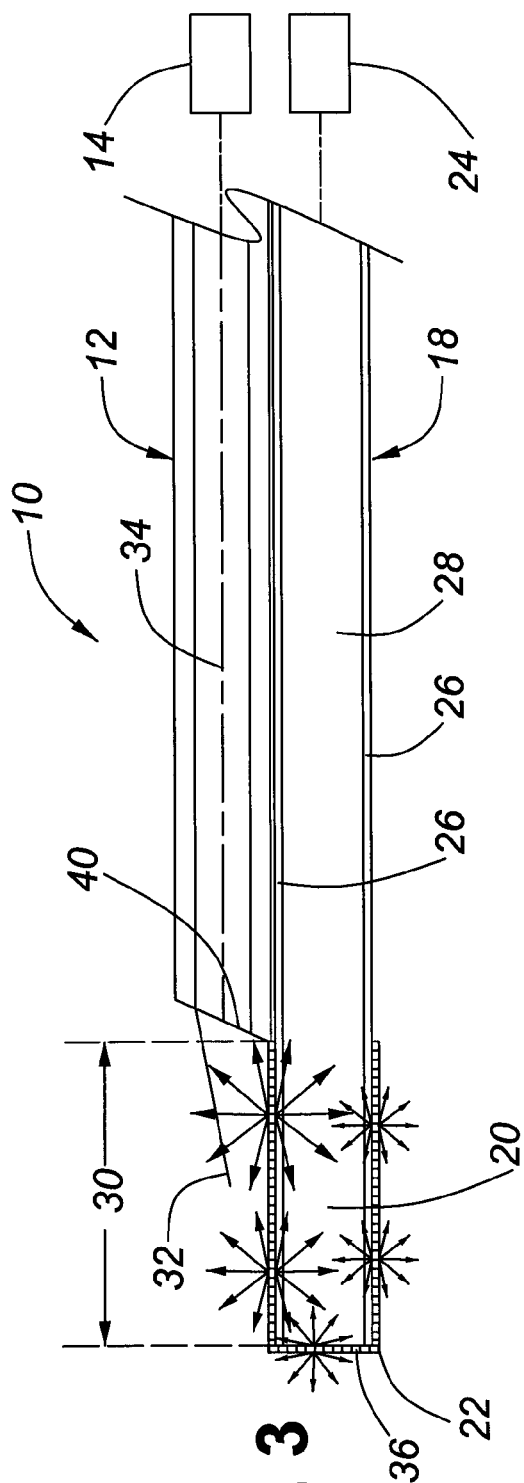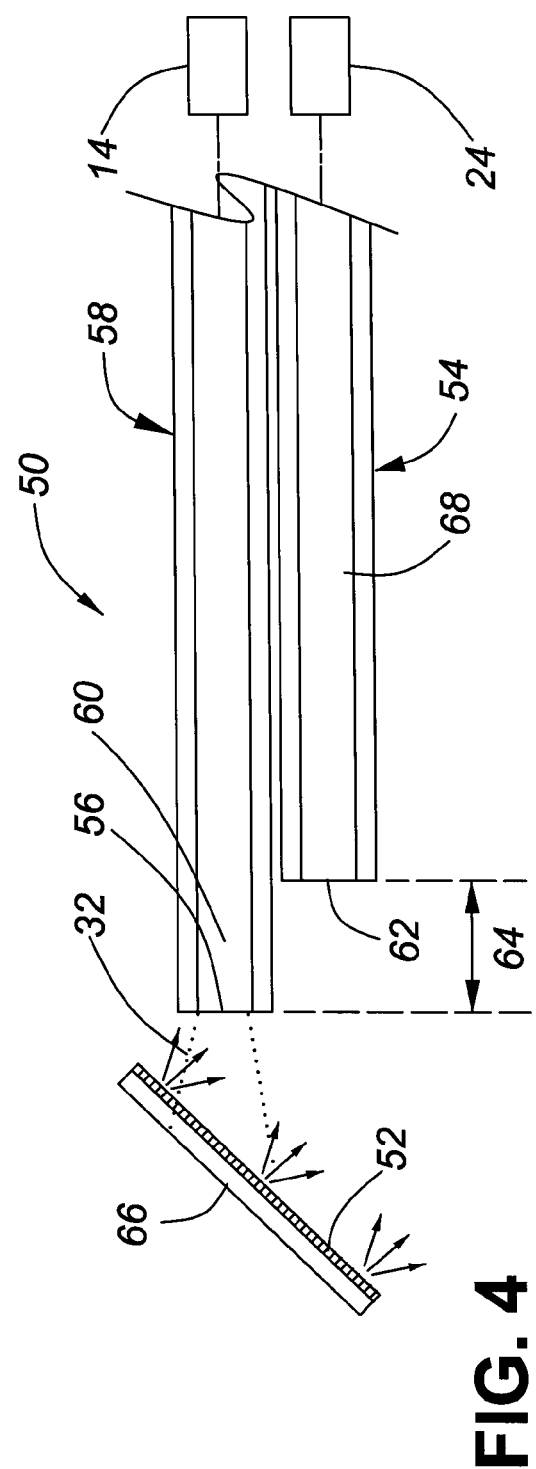

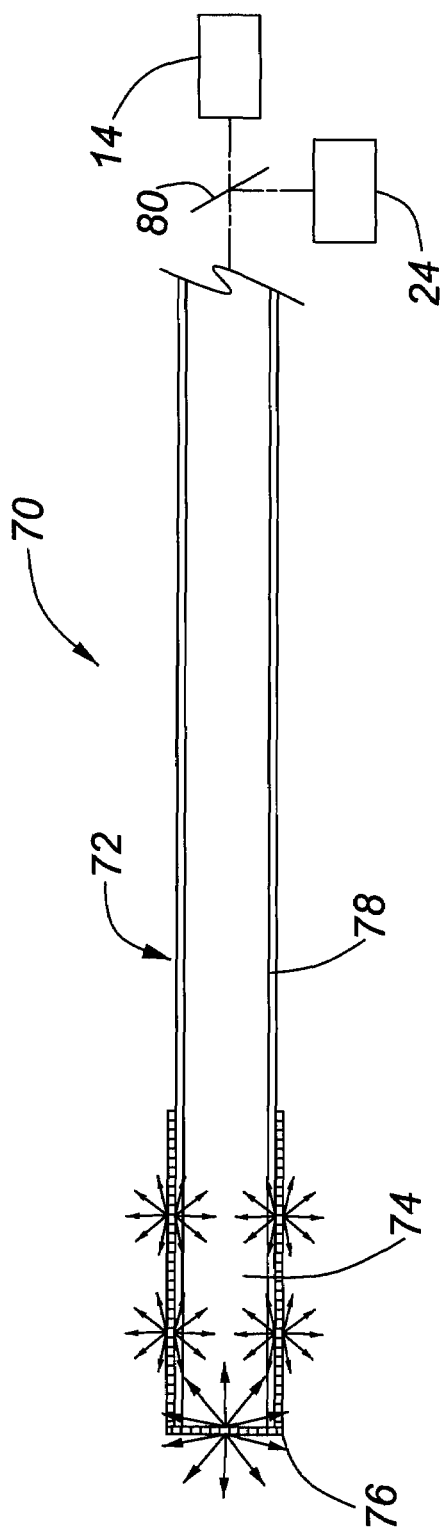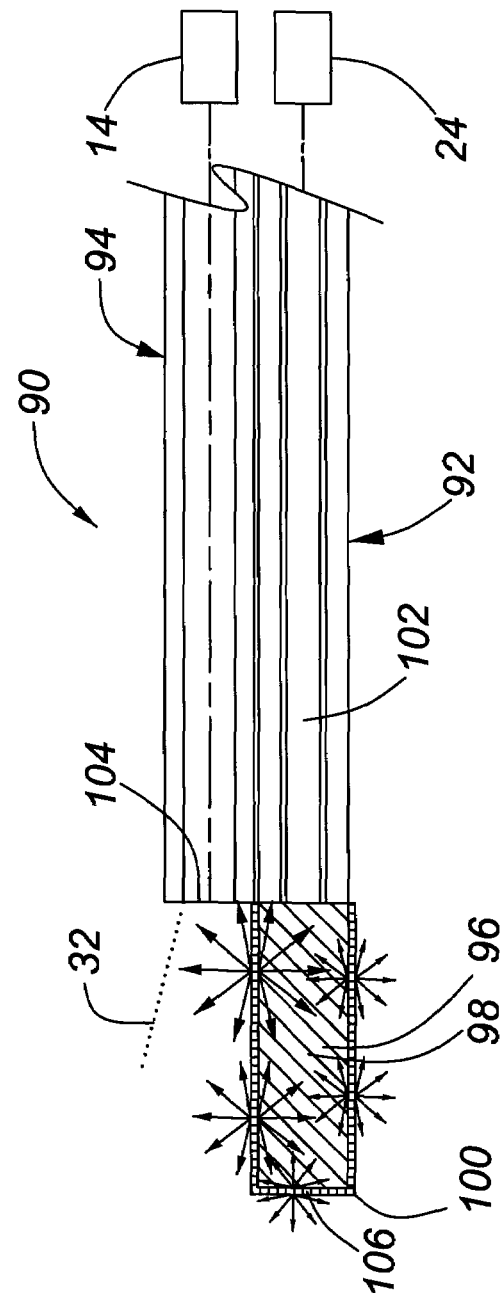
FIG. 5
FIG. 6

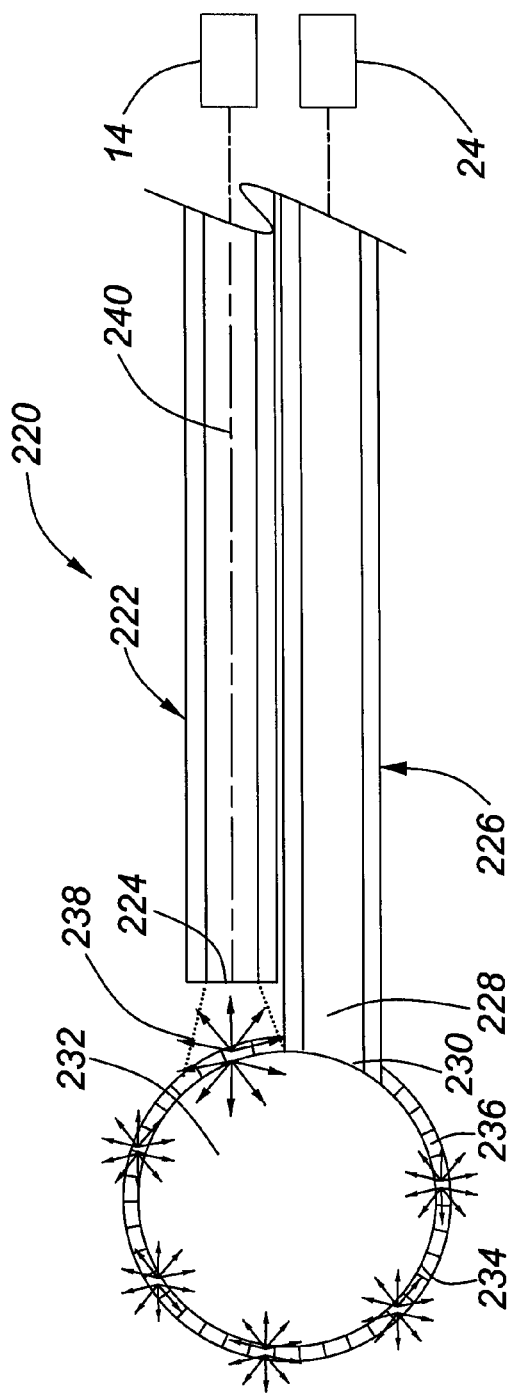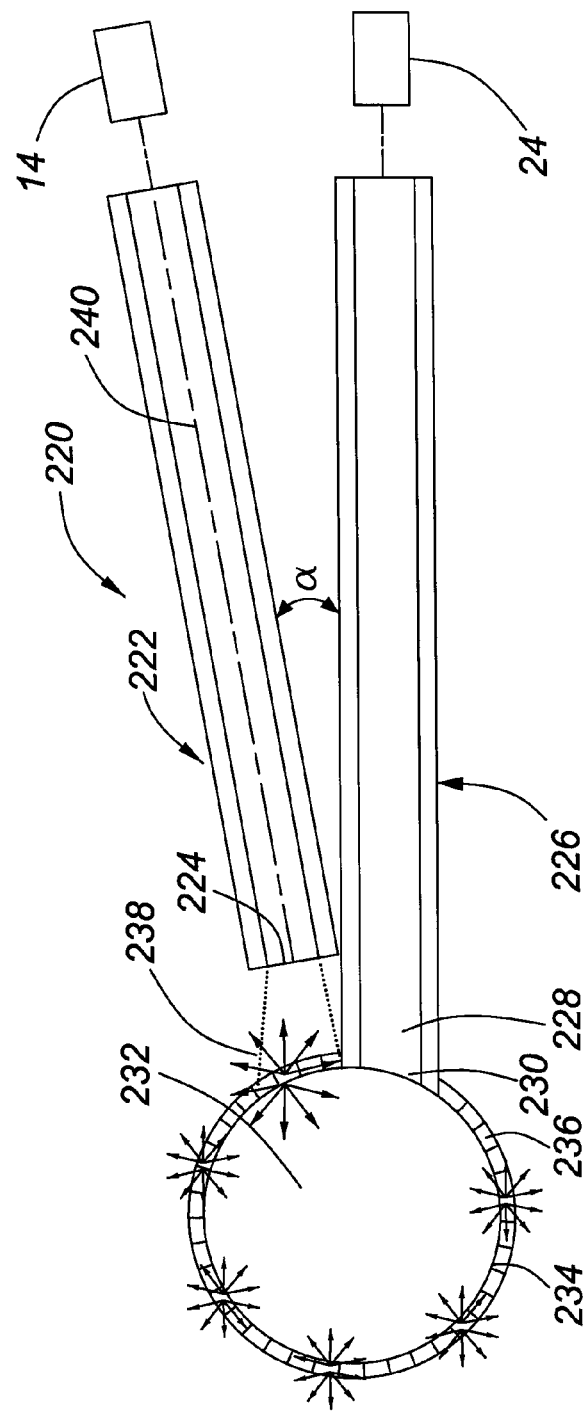

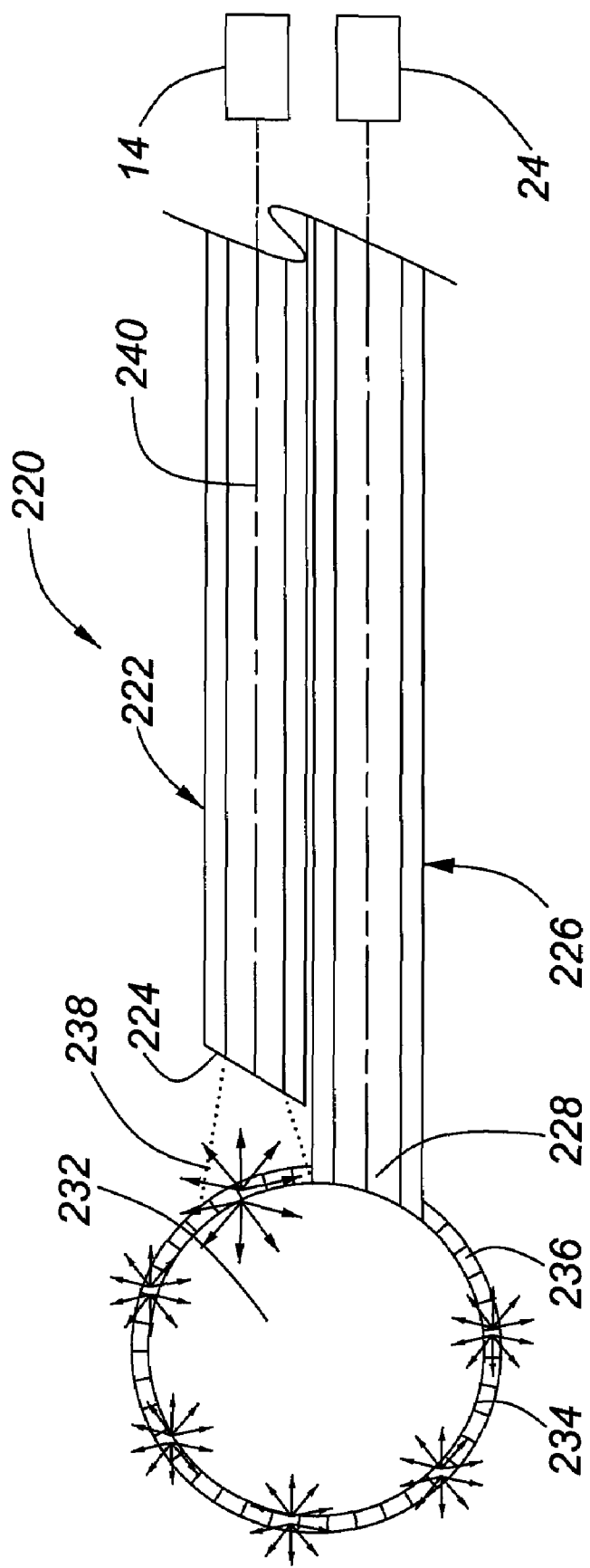

FIBER OPTIC PROBE FOR DETECTING THE PRESENCE OR ABSENCE OF ONE OR MORE SUBSTANCES WITHIN A MEDIUM

PARENT CASE TEXT

This application claims the benefit of U.S. Provisional Patent Application No. 60/788,797, filed Apr. 3, 2006, the contents of which are incorporated herein by reference.

FIELD OF THE INVENTION

The present invention relates to fiber optic probes.

BACKGROUND OF THE INVENTION

Thin film coated, intensity based fiber-optic probes for the detection of fluorescence have found many applications due to their small size and versatility. These applications include chemical research, biomedical research and clinical surgery. Other applications include waste water monitoring and explosive detection as well as the detection of leaks from containers of corrosive liquids and the like.

Fluorescent signals are usually very weak and disperse in all directions. Measurement of these signals relies heavily on the light collection efficiency of the measurement device.

A first known type of probe comprises a single optical fiber having a core covered with a film. When illuminated, the film emits light via fluorescence. Typically, the core is only covered at an end portion of the fiber (i.e. the probe tip) and light collected by the probe is measured to determine the presence of certain materials or effects. These measurements are based upon collected fluorescent light as a result of evanescent waves existing in the fiber cladding area (and beyond). The amount of collected fluorescent light will change if the refractive index of the film changes as a result of being in contact with those materials or effects (for example if the film absorbs liquid).

A second known type of probe comprises an optical fiber (or multiple optical fibers including at least one illuminating fiber and at least one receiving fiber) having a film coating attached to the end face of the receiving fiber or placed at a certain distance from its end face. Again, light collected by the probe is measured to determine the presence of certain materials or effects.

Careful consideration of the refractive index of film coatings for known probe designs is required to meet the guiding condition of the fiber. Often, the cladding of the receiving optical fiber has to be removed and replaced with certain specific materials possessing a refractive index lower than that of the fiber core material to match the guiding condition of the receiving optical fiber.

SUMMARY OF THE INVENTION

The present invention provides a fiber optic probe having a simple and rugged configuration, high light collection efficiency and improved signal-to-noise ratio. The fiber optic probe may have the objects of being relatively low cost and reusable. The improved performance of this probe facilitates traditionally difficult measurements, such as analysis of turbid waste water and low concentration explosive vapors to identify the existence of explosives.

According to a first aspect of an embodiment of the invention, there is provided a fiber optic probe for detecting the presence or absence of one or more substances within a medium. The fiber optic probe comprises at least one illuminating optical fiber for guiding excitation light from a light source to be launched from an end face of the at least one illuminating optical fiber. At least one film is provided for emitting film-emitted light when illuminated by the excitation light. The film-emitted light has a central wavelength that is different than a central wavelength of the excitation light. At least one receiving optical fiber receives and guides the film-emitted light. The at least one receiving optical fiber is a photonic crystal fiber and an end portion of the at least one receiving optical fiber is a solid segment of glass. A detector, which may consist of any conventional detector known to the art which is suitable for use in the invention, may be provided for detecting light from the receiving optical fiber.

According to a second aspect of an embodiment of the invention, there is provided a fiber optic probe for detecting the presence or absence of one or more substances within a medium. The fiber optic probe comprises at least one illuminating optical fiber for guiding excitation light from a light source to be launched from an end face of the at least one illuminating optical fiber. The fiber optic probe also comprises at least one film for emitting film-emitted light when illuminated by the excitation light, the film-emitted light having a central wavelength that is different than a central wavelength of the excitation light and at least one receiving optical fiber for receiving and guiding the film-emitted light. A lens covers at least a portion of an end of the at least one receiving optical fiber and the film covers at least a portion of an outer surface of the lens. The lens and the receiving fiber are arranged so that at least part of the film is illuminated by the excitation light. The lens may be generally spherical or any other suitable shape. Finally, the fiber optic probe also comprises a detector, which may consist of any conventional detector known to the art suitable for use in the invention, coupled to the at least one receiving optical fiber for detecting the film-emitted light.

According to a third aspect of an embodiment of the invention, there is provided a fiber optic probe for detecting the presence or absence of one or more substances within a medium. The fiber optic probe comprises at least one illuminating optical fiber for guiding excitation light from a light source to be launched from an end face of the at least one illuminating optical fiber. The fiber optic probe also comprises at least one film for emitting film-emitted light when illuminated by the excitation light. The film-emitted light has a central wavelength that is different than a central wavelength of the excitation light. At least one receiving optical fiber receives and guides the film-emitted light. The at least one receiving fiber is arranged so that an end portion of the at least one receiving fiber protrudes past the end face of the at least one illuminating fiber. The illuminating and receiving fibers may be physically joined together within a single probe structure. The respective fibers may be in side-by-side parallel relationship, either abutting or spaced apart, or alternatively may meet at an angle whereby the fibers converge towards their illuminating and receiving ends, respectively. At least part of the end portion of the at least one receiving fiber is illuminated by the excitation light. Finally, the fiber optic probe also comprises a detector which may comprise any suitable detector known to the art which is suitable for use with the invention, coupled to the at least one receiving optical fiber for detecting the film-emitted light.

According to a fourth aspect of an embodiment of the invention, there is provided a fiber optic probe for detecting the presence or absence of one or more substances within a medium. The fiber optic probe comprises at least one illuminating optical fiber for guiding excitation light from a light source to be launched from an end face of the at least one illuminating optical fiber. At least one film is provided for emitting film-emitted light when illuminated by the excitation light. The film-emitted light has a central wavelength that is different than a central wavelength of the excitation light. At least one receiving optical fiber receives and guides the film-emitted light. The film covers a thin cladding of a portion of the receiving optical fiber. The thin cladding transmits the film-emitted light into a core of the at least one receiving optical fiber. Finally, a detector, which may consist of any conventional detector known to the art which is suitable for use in the invention, is coupled to the at least one receiving optical fiber for detecting the film-emitted light.

According to a fifth aspect of an embodiment of the invention, there is provided a fiber optic probe for detecting the presence or absence of one or more substances within an immersion medium. The fiber optic probe comprises at least one illuminating optical fiber for guiding excitation light from a light source to be launched from an end face of the at least one illuminating optical fiber. An immersion medium emits immersion-emitted light when illuminated by the excitation light. The immersion-emitted light has a central wavelength that is different than a central wavelength of the excitation light. At least one receiving optical fiber is positioned alongside the at least one illuminating optical fiber for receiving and guiding the immersion-emitted light. The at least one receiving optical fiber is a photonic crystal fiber. An end portion of the at least one receiving optical fiber is a solid segment of glass. A detector, which may consist of any conventional detector known to the art which is suitable for use in the invention, is provided for detecting the immersion-emitted light from at least one receiving optical fiber.

According to a sixth aspect of an embodiment of the invention, there is provided a fiber optic probe for detecting the presence or absence of one or more substances within an immersion medium. The fiber optic probe comprises at least one illuminating optical fiber for guiding excitation light from a light source to be launched from an end face of the at least one illuminating optical fiber. An immersion medium emits immersion-emitted light when illuminated by the excitation light. The immersion-emitted light has a central wavelength that is different than a central wavelength of the excitation light. At least one receiving optical fiber is positioned alongside the illuminating optical fiber for receiving and guiding the immersion-emitted light. An end face of the at least one receiving optical fiber is aligned with the end face of the at least one illuminating optical fiber. A lens covering the end face of the at least one illuminating optical fiber and the end face of the at least one receiving optical fiber. The lens couples the immersion-emitted light into the at least one receiving optical fiber. The lens may be generally spherical or any other suitable shape. A detector, which may consist of any conventional detector known to the art which is suitable for use in the invention, is provided for detecting light from at least one receiving optical fiber.

The term "photonic crystal fiber" is intended to refer to an index-guiding type of photonic crystal fiber having a core of high refractive index surrounded by a cladding having a lower refractive index. The cladding comprises a tiny array of air-holes. Both the core and cladding of a photonic crystal fiber can be formed from the same material, e.g. pure silica.

The term "launching cone" will refer herein to the reception and launching cone of an optical fiber. The launching cone is determined by that fiber's numerical aperture as well as other conditions including the characteristics and launching conditions of the light source at the entry end of the illuminating fiber. It is also related to the fiber core and cladding sizes.

The term "standard fiber" will refer herein to any suitable type of fiber with core and cladding having different refractive indices as would be understood by a person skilled in the art.

The term "light" refers to both visible and invisible forms of electromagnetic radiation having a wavelength suitable for transmission by various types of waveguides, including optical fiber.

BRIEF DESCRIPTION OF THE DRAWINGS

An embodiment of the invention will now be described by way of example with reference to the accompanying drawings, in which:

FIG. 1 is a diagrammatic side section view of a non-limiting embodiment of the invention;

FIG. 2 is an alternative arrangement of the embodiment of FIG. 1;

FIG. 3 is another alternative arrangement of the embodiment of FIG. 1;

FIG. 4 is a diagrammatic side section view of another non-limiting embodiment of the invention;

FIG. 5 is a diagrammatic side section view of another non-limiting embodiment of the invention;

FIG. 6 is a diagrammatic side section view of another non-limiting embodiment of the invention;

FIG. 13 is a diagrammatic side section view of another non-limiting embodiment of the invention;

FIG. 14 is an alternative arrangement of the embodiment of FIG. 13;

FIG. 15 is another alternative arrangement of the embodiment of FIG. 13;

DETAILED DESCRIPTION

Figure 7:
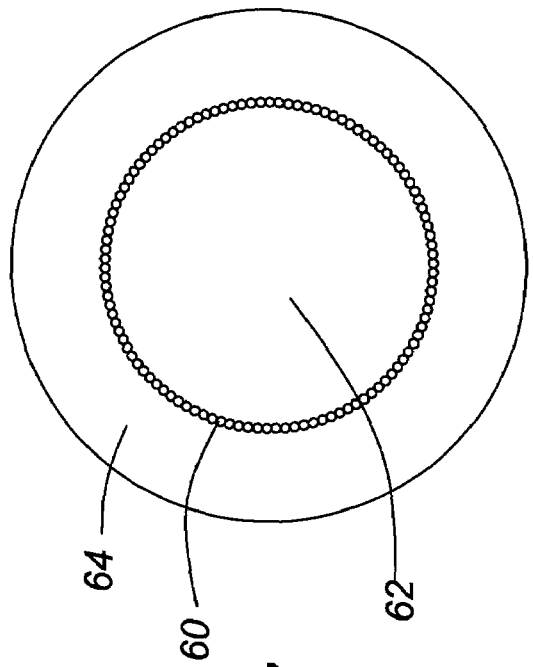
FIG. 7 illustrates a diagrammatic cross-section of an example photonic crystal fiber.

According to a non-limiting embodiment of the invention, FIG. 1 illustrates a fiber optic probe 10 comprising an illuminating optical fiber 12 (hereinafter the "illuminating fiber") for guiding excitation light from a light source 14 to be launched from an end face 16 of the illuminating fiber 12. A second, receiving optical fiber 18 (hereinafter the "receiving fiber") is arranged so that an end portion 20 of the receiving fiber 18 protrudes past the end face 16 of the illuminating fiber 12. At least part of the end portion 20 of the receiving fiber 18 is illuminated by the excitation light.

The illuminating fiber 12 and the receiving fiber 18 may be in contact with each other or spaced apart (although a higher level of effectiveness is achieved with the fibers being in close proximity or in contact).

The end portion 20 of the receiving fiber 18 is at least partly covered by a film 22 which emits light, as indicated in FIG. 1 by outwardly radiating arrows, when at least part of the film 22 is illuminated by excitation light launched from the end face 16 of the illuminating fiber 12. (Light emitted by film 22 and any other film described in this specification will be similarly indicated by outwardly radiating arrows.)

The film-emitted light has a central wavelength that is different than a central wavelength of the excitation light. Of course, it should be understood that the film-emitted light and the excitation light will both have a certain spectral width and the central wavelength is merely referred to herein as a convenient reference wavelength, as would be understood by the person skilled in the art.

The probe 10 is intended to be used in a medium for detection of the presence or absence of one more selected target substances in the medium. Typically, the medium is a liquid or gas. More specifically, the intensity and/or spectral characteristics of the light emitted by the film 22 then subsequently detected and measured by detection means 24 may be indicative of the presence of a target substance.

In this specification, light launched from the illuminating fiber 12 (and other illuminating fibers described herein) will be referred to as "excitation light". Similarly, light emitted by the film 22 (and other films described herein) will be referred to as "film-emitted light".

Film-emitted light 22 is coupled into the receiving fiber 18 and guided along the length of the receiving fiber 18 to detection means 24. The receiving fiber 18 may be connected directly to detection means 24, or via intervening optical elements such as an additional optical fiber. A detector 24 may be, for example, a spectrometer or any other light detector, typically equipped with a filter to remove stray excitation light. A suitable spectrometer is the USB2000 spectrometer with OOIBase32 software from Ocean Optics™. At will be seen that other conventional detectors or spectrometers having suitable capabilities may be used in the invention.

More specifically, the film 22 is a thin film of material which, when illuminated, emits light by fluorescence, i.e. the film material is excited by absorbing the excitation photons and emits lower-energy photons. For example, a suitable film may be a polymer having a refractive index n=1.62, which is higher than the refractive index of the fiber core material, and an emission wavelength of 642 nm which can be excited by, for example, a high power Ar+ laser with 488 nm and 514 nm emission lines. A general requirement on such a material is that is should be able to form a uniform layer of film on a glass or silica substrate or else. Examples of suitable materials are polymers, with one of them disclosed in S. M. MacKinnon and Z. Y. Wang, "*Synthesis and characterization of poly(aryl ether imide)s containing electroactive perylene diimide and naphthalene diimide units*", J. Polym. Sci., Part A: Polym. Chem., col. 38, p. 3467-3475, 2000. The formation of such a thin film layer may be achieved by means of the techniques such as spin coating. It should of course be understood that the choice of film material will depend upon the probe application and the wavelength and power of the excitation light.

As a further example, the film 22 may be a fluorescence quenching material which will emit significantly less light when in the presence of a chemical substance, for example a substance which indicates the presence of explosives, than it would if it were not in the presence of such material.

The film 22 is either applied directly to the core 28 of the receiving fiber 18 (by first stripping the cladding 26, then applying the film 22) or applied to the cladding 26 of the receiving fiber 18. If the film is applied to the cladding 26, then the cladding 26 must be sufficiently thin that light emitted by the film 22 will penetrate the cladding 26 and will be coupled into the core 28. The end face 36 may also be covered by the film 18 (as shown). For example, the receiving fiber 18 might be a CF01493-11 step index multimode fiber available from 3M™ having a core diameter of 300 μm, a cladding diameter of 330 μm and a numerical aperture of 0.37. Thus, the cladding in this example has a thickness of only 15 μm. The illuminating fiber may be a standard fiber or the same type of fiber as the receiving fiber. Of course, fibers with different core/cladding sizes may be selected. For example, fibers with smaller core and cladding sizes may be selected to reduce the size of the tip of the probe. As a further example, a receiving fiber with a larger core size will collect a larger amount of film-emitted light.

Where the film is applied directly to the core 28, the dead space between the illuminating fiber 12 and the receiving fiber 18 is not significant, as the excitation light will illuminate the film directly. Similarly, keeping the cladding 26 of the receiving fiber 18 thin will also keep the dead space between them relatively small. The amount of film-emitted light collected by the receiving fiber increases as the dead space is decreased, thus enhancing the light collection efficiency of the probe 10. The light collection efficiency refers to the ratio of the amount of light emitted by the film 22 to the amount of light coupled into the core 28 of the receiving fiber 18 (subsequently detected by the detection means 24). By increasing the light collection efficiency, a significant reduction in integration time can be achieved (approximately 20 times lower in comparison with the performance of a probe comprising two fibers with aligned end faces and a tilted film placed in front of the fibers).

The thickness of the film 22 depends on many factors, including the absorption of excitation light for a particular material and the quantum yield of the material (i.e. the percentage of excitation photons which are converted to fluorescence photons). The thickness should be carefully controlled as the signal-to-noise ratio of the signal detected by the detection means 24 depends upon the film thickness. A very thin film will cause more stray excitation light to penetrate into the receiving fiber, thereby increasing noise. Similarly, a very thick film will deliver very limited excitation light into the area close to the fiber core. As such, there will be an optimum film thickness for the probe taking into account the fiber geometry, choice of film material and so on.

The signal-to-noise ratio of the detected signal also depends upon a separation or retreat length 30, i.e. the length of the end portion 20 of the receiving fiber 18 which protrudes past the end face 16 of the illuminating fiber 12. The separation 30 and the thickness of the film 22 can each be adjusted to optimize the signal-to-noise ratio. Of course, the signal-to-noise ratio is also dependent upon other factors, such as the quality of the beam formed by the light coupled into the receiving fiber 18 from the film 22, as would be understood by the person skilled in the art.

As shown in FIG. 1, the illuminating fiber 12 and the receiving fiber 18 are in side-by-side parallel relation. The launching cone 32 of the illuminating fiber 12 will be generally symmetric about the optical axis 34 of the illuminating fiber 12.

Alternatively, as shown in FIG. 2, the illuminating fiber 12 may be disposed at a non-parallel angle α from the receiving fiber 18 to 'bend' or direct the launching cone 32 of the illuminating fiber 12 towards the film 22. By directing the launching cone 32 of the illuminating fiber 12 towards the film 22, the intensity of light impinging upon the film 22 will be increased and the amount of light emitted by the film 22 and coupled into the receiving fiber 18 will increase. This angle α can range anywhere from about 0° to about 90°.

Alternatively, as shown in FIG. 3, the end face 16 of the illuminating optical fiber 12 can be cut or polished at an angle to 'bend' or direct the launching cone 32 of the illuminating fiber 12 towards the film 22. As explained previously, by directing the launching cone 32 of the illuminating fiber 12 towards the film 22, the intensity of light impinging upon the film 22 will be increased and the amount of light emitted by the film 22 and coupled into the receiving fiber 18 will also be increased.

While in FIGS. 1, 2 and 3, the end face 36 of the receiving fiber 18 is flat, it may be angled (either cut or polished) to reduce back reflection. The end face 36 may also be covered by high refractive index material to reduce back reflection. Alternatively, the end portion 20 of the receiving fiber 18 may be tapered to further increase the light collection efficiency.

In accordance with another non-limiting embodiment of the invention, FIG. 4 illustrates a fiber optic probe 50 which is generally similar to the fiber optic probe 10 as illustrated in FIG. 1 but in which a film 52 does not cover the cladding of the receiving fiber 54 but rather is provided on a separate member spaced from the end face 56 of the illuminating fiber 58 and positioned to receive light from the illuminating fiber 58. The end portion 60 of the illuminating fiber 58 protrudes past the end face 62 of the receiving fiber 54 (by a protrusion length 64). The illuminating and receiving fibers may be standard fibers. Alternatively, the end faces of the fibers may be aligned. The end faces of the fibers may be angle polished to improve light collection efficiency. The end portion of the receiving fiber may be tapered to improve light collection efficiency.

The film 52 may be, for example, a solid film or a film coating on a glass slide 66. The film 52 is disposed at an angle (e.g. 37° to the fiber end face) to the end face 62 of the receiving fiber 54. Light emitted by the film 52 is coupled into the core 68 of the receiving fiber 54 via the end face 62 of the receiving fiber 54. The coupling efficiency of this probe is optimized at certain values of the protrusion length 64.

The thickness of the film 52 may be larger than the thickness of the film 22 described previously.

Figure 20:
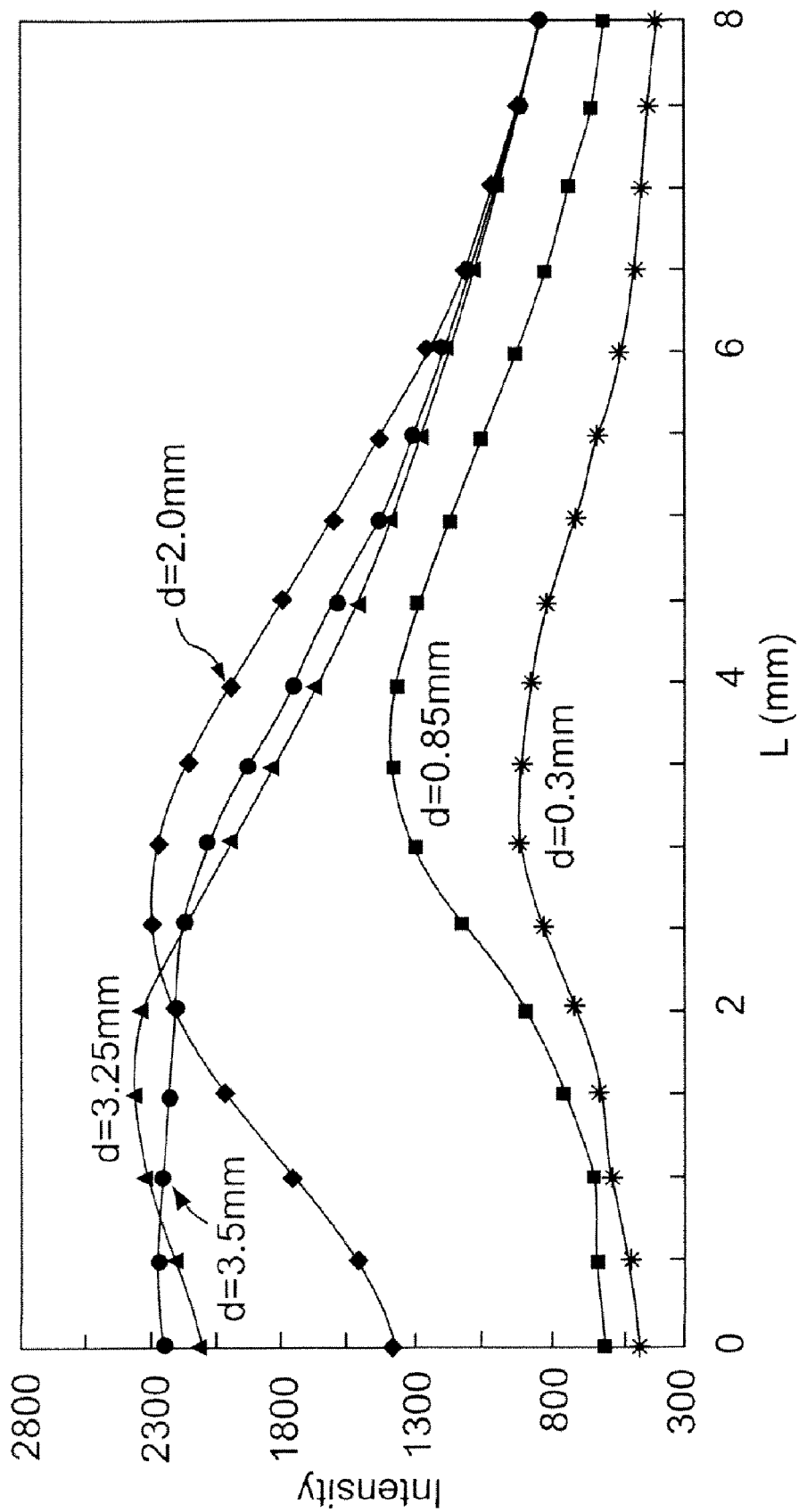
FIG. 20 is a graph of intensity of film-emitted light measured as a function of protrusion length L for a number of film positions (d).

Measurements of the intensity of film-emitted light measured by the detection means 24 are shown in FIG. 20. For these measurements, the protrusion length 64 (L) was varied for a number of positions of the film 52, where the position of the film 52 is set out as the separation (d) of the film from the end face of the illuminating fiber (as the film is tilted, d is measured from the end of the film closest to the illuminating fiber). The film 52 used in these experiments had a fluorescent emission wavelength (central wavelength) of 642 nm. The maximum relative collection efficiency $^d\eta_{max}$ associated with each film position is given by $$^d\eta_{max}(\%) = \frac{^dI_{F-max}(L \neq 0) - ^dI_F(L = 0)}{^dI_{F-max}(L \neq 0)}$$

where $^dI_{F-max}(L\neq 0)$ is the maximum fluorescent intensity received by the spectrometer for each separation d, $^dI_F(L=0)$ is the fluorescent intensity received by the spectrometer when the receiving fiber aligned with the illuminating fiber. As is clearly shown, the maximum relative collection efficiency value $^d\eta_{max}$ occurs at non-zero values of the retreat length L. As is also clearly shown, the relative collection efficiency decreases again after the protrusion length (L) reaches that maximum value.

In accordance with another non-limiting embodiment of the invention, FIG. 5 illustrates a fiber optic probe 70 comprising a single optical fiber 72 which acts as both an illuminating fiber and a receiving fiber. This embodiment might be particularly advantageous for applications where small size is desirable. An end portion 74 of the fiber 72 is at least partly covered by a film 76 which is similar to the films described previously. As described previously with respect to the non-limiting embodiment of FIG. 1, the film 76 at least partially covers the thin cladding 78 and/or end face of the fiber 72. Of course, if the cladding 78 the removed (as described previously with reference to FIG. 1), the film 76 will cover the side wall of the core. The end face of the fiber may be angle polished and covered by a high refractive index material to reduce back reflections, as described previously with reference to the receiving fiber of FIGS. 1, 2 and 3. The end portion 74 of the fiber 72 may be tapered to further increase the light collection efficiency.

For the single-fiber probe 70, the detection means 24 may also comprise a beam splitter 80 in order to separate the excitation light and the film-emitted light. The beam splitter 80 will be placed between the source 14 and the input end of the fiber 72 to pass the excitation light and reflect the film-emitted light. An additional filter may be placed before the detection means 24 to remove any stray light. The beam splitter 80 may be a dichroic beam splitter to effectively separate the excitation light and the film-emitted light.

In the absence of direct illumination, or in combination with direct illumination (when the environment surrounding the probe is reflective), the film 76 will be excited by evanescent light formed by the higher order modes propagating along the fiber 72. As the amount of energy in the higher order modes of the fiber 72 is much less than the amount of energy in the lower order modes, the amount of evanescent light is quite small and the detected signal will be weaker than the signal produced by the non-limiting embodiments described previously (i.e. considering the same intensity level of excitation light from the source 14).

At least a thin layer of the film 76 (on the order of a wavelength) which is close to the surface of the thin cladding 78 or the side wall of the fiber core will interact with the evanescent light. The evanescent light will only excite the film 76 within the thickness of approximately one wavelength. The signal is free from the interference beyond this thickness.

In accordance with another non-limiting embodiment of the invention, FIG. 6 illustrates a fiber optic probe 90 of similar geometry to the fiber optic probe 10 illustrated in FIG. 1, but wherein the receiving optical fiber 92 is a photonic crystal fiber. The illuminating fiber 94 may also be a photonic crystal fiber.

Through a thermal fusing process (using, for example, a fiber splicer), a segment of air holes at an end portion 96 of the receiving fiber 92 may be sealed together to form a segment 98 of solid glass. The segment 98 is at least partly covered by a film 100 (similar to the films described previously). Light emitted by the film 100 will pass though the segment 98 to the core 102 of the receiving fiber 92. This segment of glass improves the light collection efficiency of the probe. The length of the segment 98 may be optimized (the optimum length will depend upon a number of factors including, but not limited to, the fiber type).

FIG. 7 illustrates a cross-section of a suitable photonic crystal fiber having a high numerical aperture. The cladding 60 of this fiber comprises a plurality of air holes. The air holes approximate the index of refraction of air (n≈1). Light is guided within the core 62. The cladding 60 is surrounded by a layer 64, which is the same material as the fiber core. It should be understood that other types of photonic crystal fibers would be suitable for this application and the fiber illustrated in FIG. 7 is merely an example. The fiber illustrated in FIG. 7 is similar to the MM-HN-200 PCF available from Crystal-Fiber A/S.

Referring back to FIG. 6, the illuminating fiber 94 of the probe 90 may be angled with respect to the receiving fiber 92, as described previously with reference to the non-limiting embodiment illustrated in FIG. 2. Likewise, the end face 104 of the illuminating fiber 94 may be cut or polished at an angle, as described previously with reference to the non-limiting embodiment illustrated in FIG. 3. Similarly, the end face 106 of the receiving fiber 92 may be cut or polished at an angle and covered by a high refractive index material, as described previously with reference to the non-limiting embodiment illustrated in FIGS. 1, 2 and 3. Further, the end portion 96 of the receiving fiber 92 may be tapered to further increase the light collection efficiency.

Figure 8:
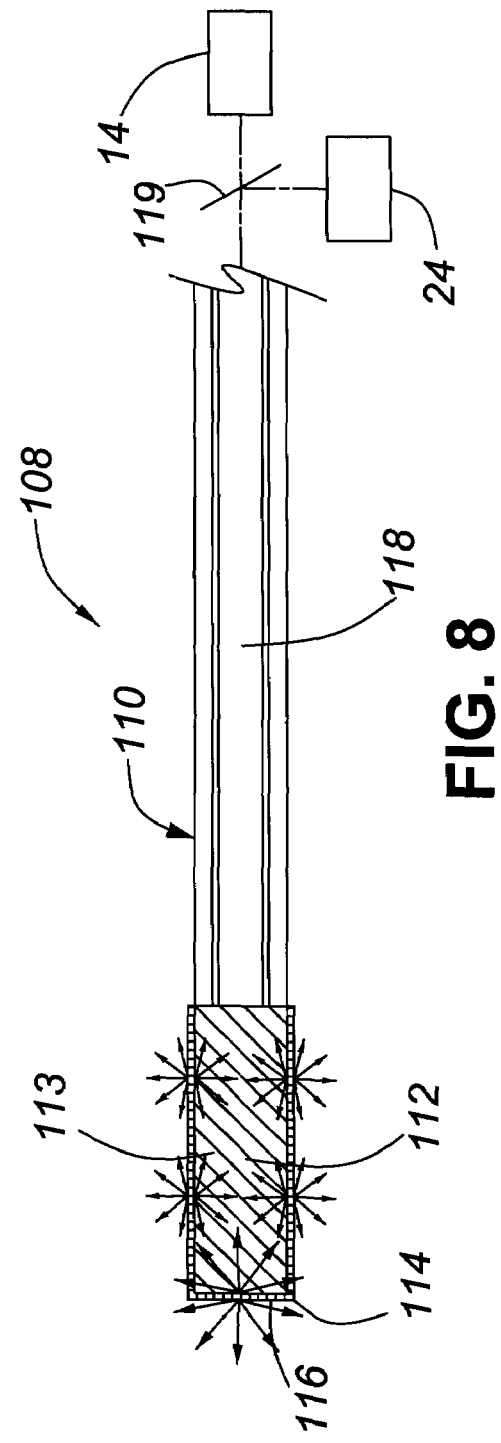
FIG. 8 is a diagrammatic side section view of another non-limiting embodiment of the invention.

According to another non-limiting embodiment of the invention, FIG. 8 illustrates fiber optic probe 108 comprising a single photonic crystal fiber 110. The end portion 112 of the fiber 110 is fused to form a solid glass segment 113 (similar to segment 98 described previously) which is at least partly covered with a film 114. Excitation light propagating along the fiber 110 from the source 14 will encounter the segment 113. Light emitted by the film 114 will pass though the segment 113 to the core 118 of the fiber 114 without significant attenuation. Any suitable length of segment 112 may be used. Improved signal quality may be achieved by angle polishing the end face 116 and coating it with a high refractive index figure. The end portion 112 of the fiber 110 may be tapered to further increase the light collection efficiency.

As in FIG. 5, the detection means 24 of FIG. 8 may also comprise a beam splitter 119 in order to separate the excitation light and the film-emitted light. The beam splitter 119 will be placed between the source 14 and the input end of the fiber 72, as described previously.

Figure 9:
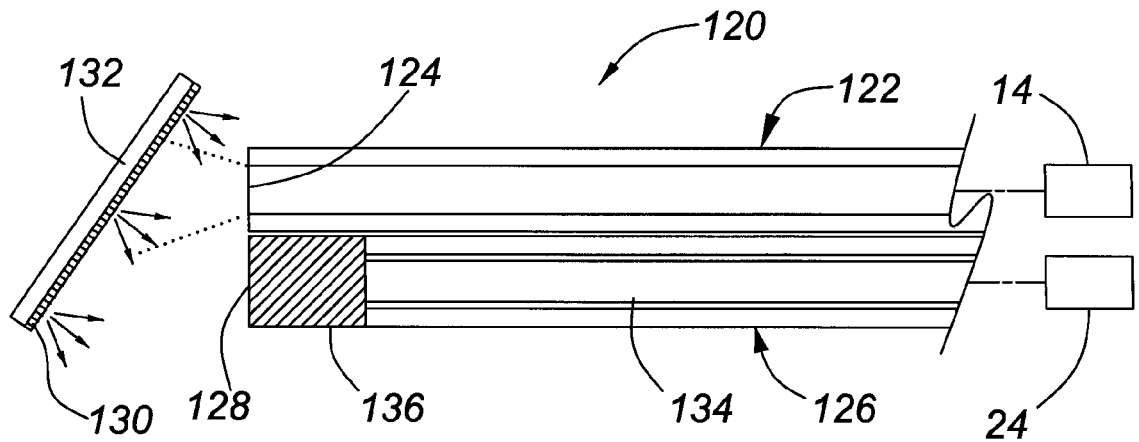
FIG. 9 is a diagrammatic side section view of another non-limiting embodiment of the invention.

According to another non-limiting embodiment of the invention, FIG. 9 illustrates a fiber optic probe 120 comprising an illuminating fiber 122 for guiding excitation light from a light source 14 to be launched from an end face 124 of the illuminating fiber 122 and a second, receiving fiber 126 positioned alongside illuminating fiber 122. The receiving fiber 126 is a photonic crystal fiber. The illuminating fiber 122 may also be a photonic crystal fiber. The end face 128 of receiving fiber 126 and the end face 124 of illuminating fiber 122 are generally aligned, as shown. Alternatively, there may be a separation between the end face 128 of receiving fiber 126 and the end face 124 of illuminating fiber 122.

A film 130 is spaced from the end faces 124 and 128 of the illuminating fiber 122 and the receiving fiber 126, respectively. The film 130 is similar the other films described previously, and may be applied in a similar way to film 52 as a solid film or a film coating on a glass slide 132.

Light emitted by the film 130 is coupled into the core 134 of the receiving fiber 126 via the end face 128 of the receiving fiber 126. The end portion 136 of the receiving fiber 126 is fused to form a solid glass segment (as described previously with reference to FIG. 6) so that the light collection efficiency of the probe 120 is enhanced. The end face 128 of the receiving fiber 126 may be cut or polished at an angle to enhance light collection efficiency of the probe. The illuminating fiber 122 may also be a photonic crystal fiber which may have a fused end portion as well (and may be cut or polished at an angle as well).

In experiments comparing the performance of a receiving fiber 126 having a segment 136 and a receiving fiber 126 having no such segment, an improvement in collection efficiency was greatly improved (on the order of 55%). Also, a receiving fiber 126 having a longer segment 136 of glass has a higher collection efficiency than a receiving fiber 126 having a shorter segment 136.

This effect can be described conceptually with reference to the projections of the light reception and launching cones of the illuminating fiber 122 and the receiving fiber 126, respectively. These projections are sometimes referred to as fields of view and have an elliptical shape when projected on the titled film 130. The field of view of the fiber having a segment 136 is larger than the field of view of a fiber having no such segment. The distance between the center of the field of view (or Fresnel diffraction field) of the illuminating fiber and the center of the field of view of the receiving fiber determines how much of the film-emitted light will be coupled into the receiving fiber. Thus, if the field of view of a fiber having a segment 136 is larger, the overlap will be greater and the light collection efficiency of the probe will be enhanced. However, there will obviously be an upper limit to the size of the segment 136. There will be an optimum segment length for each fiber type, separation of film 130, and so on. For example, in an embodiment similar to that illustrated in FIG. 9, the optimum segment length is on the order of three times the cladding diameter of the receiving fiber.

It should be noted that the size of the field of view of the illuminating fiber depends upon a number of factors including the light intensity distribution at the end face 124 of the illuminating fiber 122 (which is in turn determined by the source 14 and the launching conditions at the entry end of the illuminating fiber 122). This field of view is also related to the fiber core and cladding sizes. The field of view of the receiving fiber 126 is determined by the smaller angle of the maximum reception angle of the receiving fiber 126 and the maximum acceptance angle of the detection means 24.

Figure 10:
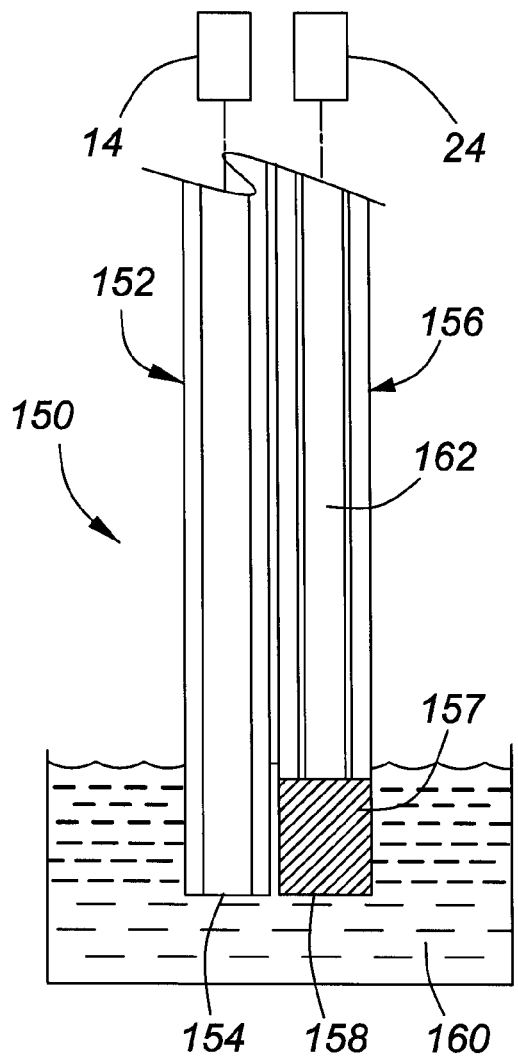
FIG. 10 is a diagrammatic side section view of another non-limiting embodiment of the invention.

According to another non-limiting embodiment of the invention, FIG. 10 illustrates a fiber optic probe 150 comprising an illuminating fiber 152 for guiding excitation light from a light source 14 to be launched from an end face 154 of the illuminating fiber 152 and a second, receiving fiber 156 positioned alongside illuminating fiber 152. The receiving fiber 156 is a photonic crystal fiber. The illuminating fiber 152 may also be a photonic crystal fiber. The end face 158 of receiving fiber 156 and the end face 154 of illuminating fiber 152 are generally aligned.

The probe 150 may be used in a liquid immersion medium 160. Liquid immersion media which emit light by fluorescence are known. For example, a suitable liquid immersion medium could be Alexa Fluor™ 635 dye conjugate diluted in a 0.1 M phosphate-buffered saline (PBS), the PBS liquid containing 0.1 M NaCl and 2 mM $N_3Na$ and having a pH value of 7.5. This dye may be excited by a suitable source, such as a He—Ne laser operating at 633 nm, to fluoresce at 647 nm (central wavelength). It should be noted that light collection efficiency of the probe will increase for higher concentrations of the liquid immersion sample. It should also be noted that the immersion medium may emit light by another process, such as Raman scattering.

Light emitted by the immersion medium 160 is coupled into the core 162 of the receiving fiber 156 via the end face 158 of the receiving fiber 156. In order to optimize this coupling, the receiving fiber 156 has a fused end portion 157 as described previously with reference to FIG. 6. The end face 158 of the receiving fiber 156 and/or the illuminating fiber 152 may also be cut or polished at an angle. This glass segment will convert at least part of the dead zone immediately in front of the probe to an active volume. This can be explained conceptually in a similar fashion to the example embodiment of FIG. 9. Here, the volume overlap of the light reception and launching cones is increased by fusing the end portion 157 of the receiving fiber 156 which results in an increase in the amount of light collected by the receiving fiber 156. It should be noted that the glass segment, and other similar glass segments described herein will have extremely low attenuation. This is particularly beneficial when operating the probe 150 in an immersion medium having a higher level of attenuation and/or absorption. More specifically, it allows immersion-emitted light to travel a shorted path to reach the fiber core (which is difficult to achieve with conventional fiber). Similarly, if the measurement volume of the medium is very small, the enhanced light collection efficiency of the probe 150 will provide a strong enough signal to offer useful measurements.

The fused end portion 157 of the receiving fiber will also prevent the uptake of fluid into the air holes of the photonic crystal fiber(s) by capillary action. This is particularly advantageous for chemical or biological sensing where the fiber is in contact with fluids. Uptake of fluid can drastically change the optical properties of the fiber.

Figure 11:
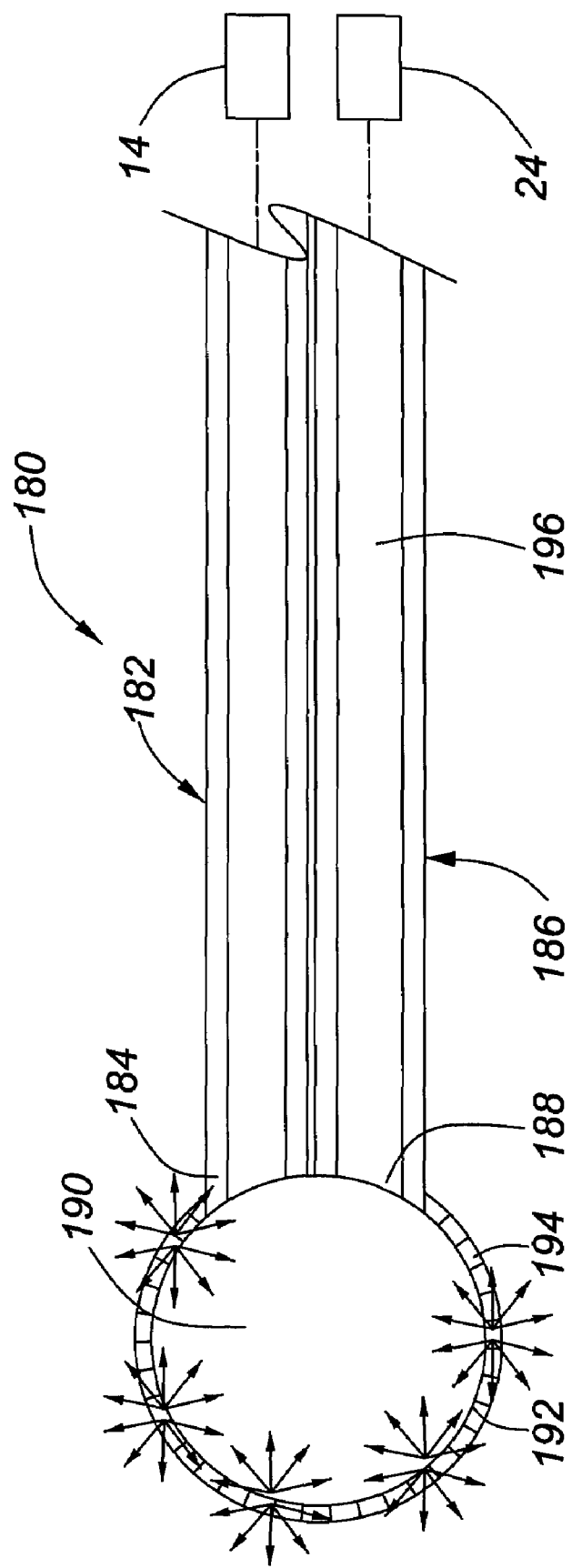
FIG. 11 is a diagrammatic side section view of another non-limiting embodiment of the invention.

According to another non-limiting embodiment of the invention, FIG. 11 illustrates a fiber optic probe 180 comprising an illuminating optical fiber 182 for guiding excitation light from a light source 14 to be launched from an end 184 of the illuminating fiber 182. A second, receiving fiber 186 is positioned alongside illuminating fiber 182. Both fibers can be standard fibers.

The end 188 of the receiving fiber 186 and the end 184 of illuminating fiber 182 are generally aligned and are covered by a shared lens 190. The lens 190 may be formed by fusing or heating the end 188 of the receiving fiber 186 and the end 184 of illuminating fiber 182. Alternatively, the lens 190 may be glued to the end 188 of the receiving fiber 186 and the end 184 of illuminating fiber 182.

It should be noted that this lens 190 and other lenses referred to in this specification may be of many shapes, as would be understood by the person skilled in the art. This type of lens is sometimes referred to as a micro lens. The formation of such lenses involves a reshaping of the fiber tip by fusing or heating the end, as mentioned previously. For example, a so-called 'ball lens' which approximates a spherical lens may be formed. The focusing effect of the lens will depend upon the size and shape of the lens.

At least a portion of an outer surface 192 of the lens 190 is covered by a film 194 which is similar to the films described previously. Excitation light launched from the illuminating fiber 182 will illuminate the at least part of the film 194. The film 194 will emit light, as described previously, which will be coupled into the receiving fiber 186 via the lens 190. After being excited by the illuminating light, the film-emitted light will travel inside the lens 190 and experience multiple internal reflections at the boundary of the lens 190 and the film 194. A portion of that film-emitted light is received by the receiving fiber 186 and guided along the length of the receiving fiber 186 to detection means 24.

The thickness of the film 194 will be controlled to optimize the signal to noise ratio. Light emitted by the film 194 will pass through the lens 190 into the core 196 of the receiving fiber 186 without significant attenuation, thus enhancing the light collection efficiency of the probe 180.

Figure 12:
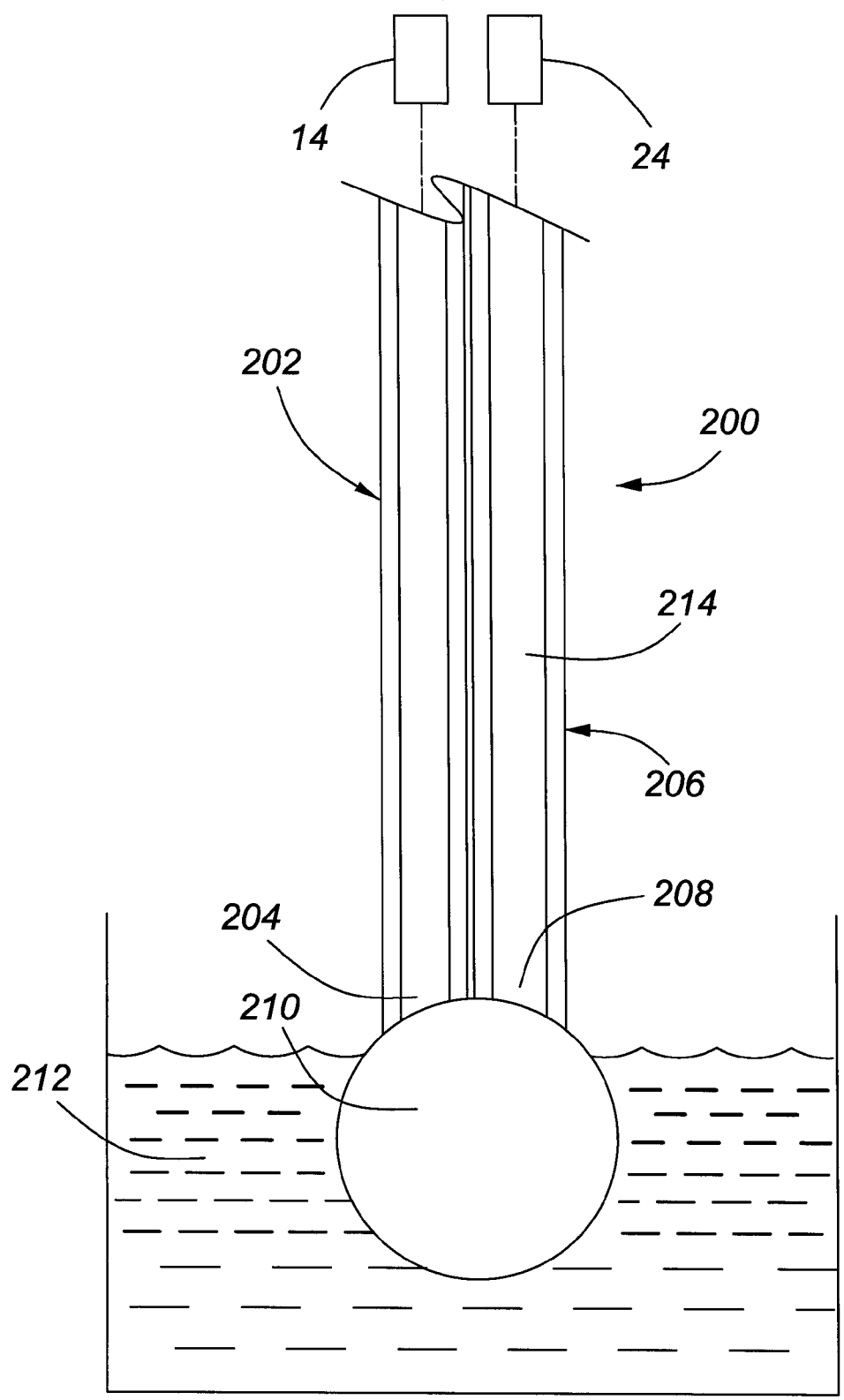
FIG. 12 is a diagrammatic side section view of another non-limiting embodiment of the invention.

According to another non-limiting embodiment of the invention, FIG. 12 illustrates a fiber optic probe 200 comprising an illuminating optical fiber 202 for guiding excitation light from a light source 14 to be launched from an end 204 of the illuminating fiber 202. A second, receiving fiber 206 is positioned alongside illuminating fiber 202.

The end 208 of the receiving fiber 206 and the end 204 of illuminating fiber 202 are generally aligned and are covered by a shared lens 210, similar to the lens 190 described previously (without the film 194). The probe 200 may be used in a liquid immersion medium 212 similar to the liquid immersion medium 160 described previously with reference to FIG. 10. Light emitted by the immersion medium 212 is coupled into the core 214 of the receiving fiber 206 via the lens 210. Both fibers can be standard fibers.

According to another non-limiting embodiment of the invention, FIG. 13 illustrates a fiber optic probe 220 comprising an illuminating fiber 222 for guiding excitation light from a light source 14 to be launched from an end face 224 of the illuminating fiber 222. A second, receiving fiber 226 is arranged so that an end portion 228 of the receiving fiber 226 protrudes past the end face of the illuminating fiber 222. Both fibers can be standard fibers.

At least a portion of the end 230 of the receiving fiber 226 is covered by a lens 232. The lens 232 may be formed by fusing or heating the end face 230 of the receiving fiber 226. Alternatively, the lens 232 may be glued to the end 230 of the receiving fiber 226. At least a portion of an outer surface 234 of the lens 232 is covered by a film 236 which is similar to the films described previously. Excitation light emitted from an end face 224 of the illuminating fiber 222 will illuminate at least part of the film 236. The film will emit light, as described previously with reference to lens 190, which will be coupled into the receiving fiber 226 via the lens 232.

The lens 232 is preferably formed or attached in such a way that it extends towards the end face 224 of the illuminating optical fiber 222, as shown, to optimize illumination of the film 236 by the illuminating optical fiber 222.

As shown in FIG. 13, the illuminating fiber 222 and the receiving fiber 226 are in side-by-side parallel relation. The launching cone 238 of the illuminating fiber 222 will be generally symmetric about the optical axis 240 of the illuminating fiber 222.

Alternatively, as shown in FIG. 14, the illuminating fiber 222 may be disposed at a non-parallel angle α from the receiving fiber 226 to 'bend' or direct the launching cone 238 of the illuminating fiber 222 towards the film 236. By directing the launching cone 236 of the illuminating fiber 222 towards the film 236, the intensity of light impinging upon the film 236 will be increased and the amount of light emitted by the film 236 and coupled into the receiving fiber 226 will increase. This angle α can range anywhere from about 0° to about 90°.

Alternatively, as shown in FIG. 15, the end face 224 of the illuminating optical fiber 222 can be cut or polished at an angle to 'bend' or direct the launching cone 238 of the illuminating fiber 222 towards the film 236. As explained previously, by directing the launching cone 238 of the illuminating fiber 222 towards the film 236, the intensity of excitation light impinging upon the film 236 will be increased and the amount of light emitted by the film 236 and coupled into the receiving fiber 226 will increase.

Figure 16:
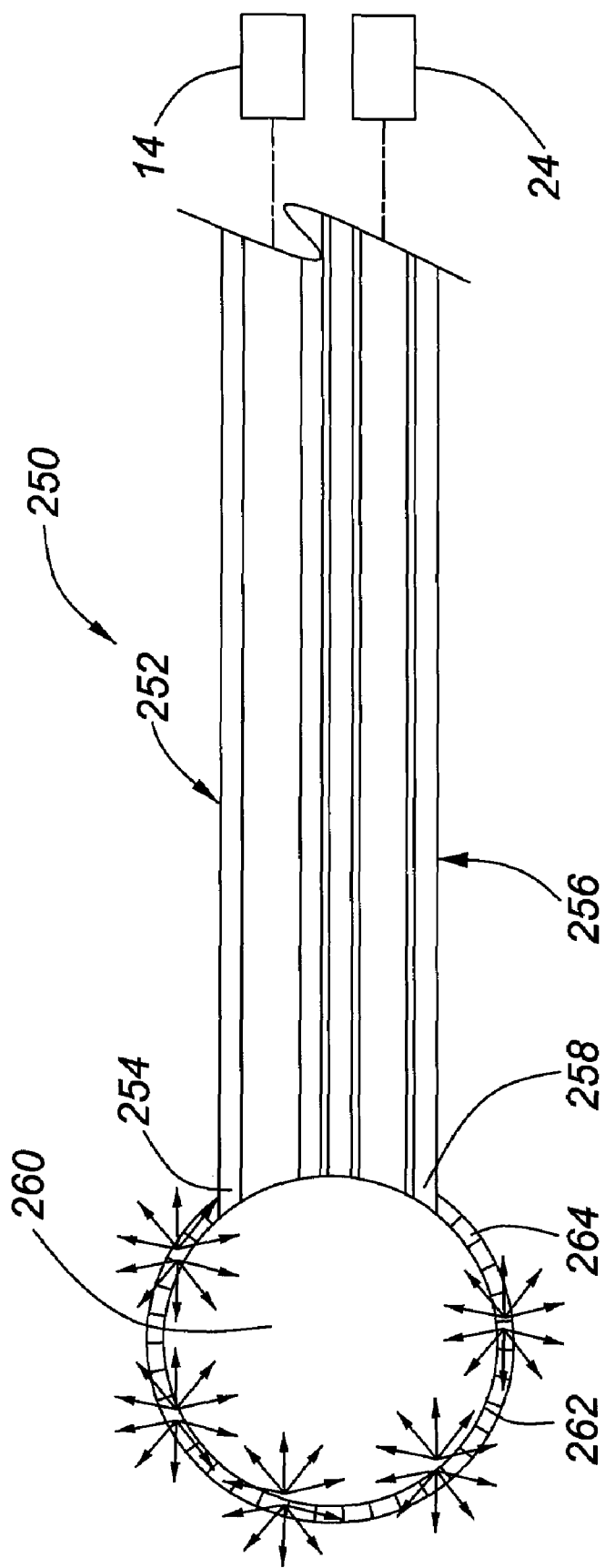
FIG. 16 is a diagrammatic side section view of another non-limiting embodiment of the invention.

According to another non-limiting embodiment of the invention, FIG. 16 illustrates a fiber optic probe 250 comprising an illuminating optical fiber 252 for guiding excitation light from a light source 14. A second, receiving fiber 256 is positioned alongside illuminating fiber 252. The illuminating fiber 252 and/or the receiving fiber 256 may be photonic crystal fibers, similar to the photonic crystal fibers described previously. The illuminating fiber may also be a standard fiber.

The end 258 of the receiving fiber 256 and the end 254 of illuminating fiber 252 are generally aligned and are covered by a shared lens 260. The shared lens 260 may be formed by fusing or heating the end face 254 of the illuminating fiber 252 and the end face 258 of the receiving fiber 256 (or glued thereto, as described previously with regard to other embodiments having a lens). Fusing or heating the end faces of the fibers will also seal the air holes. At least a portion of an outer surface 262 of the lens 260 is covered by a film 264 which is similar to the films described previously. Excitation light launched from an end 254 of the illuminating fiber 252 will illuminate the film 264. The film will emit light, as described previously, which will be coupled into the receiving fiber 256 via the lens 260. After being excited by the illuminating light, the film-emitted light will travel inside the lens and experience multiple internal reflections at the boundary of the lens and the film. A portion of that film-emitted light is eventually received by the receiving fiber 256.

The probe 250 may be used in a liquid immersion medium similar to the liquid immersion medium 160 described previously with reference to FIG. 12 (without the film 264, of course).

Figure 17:
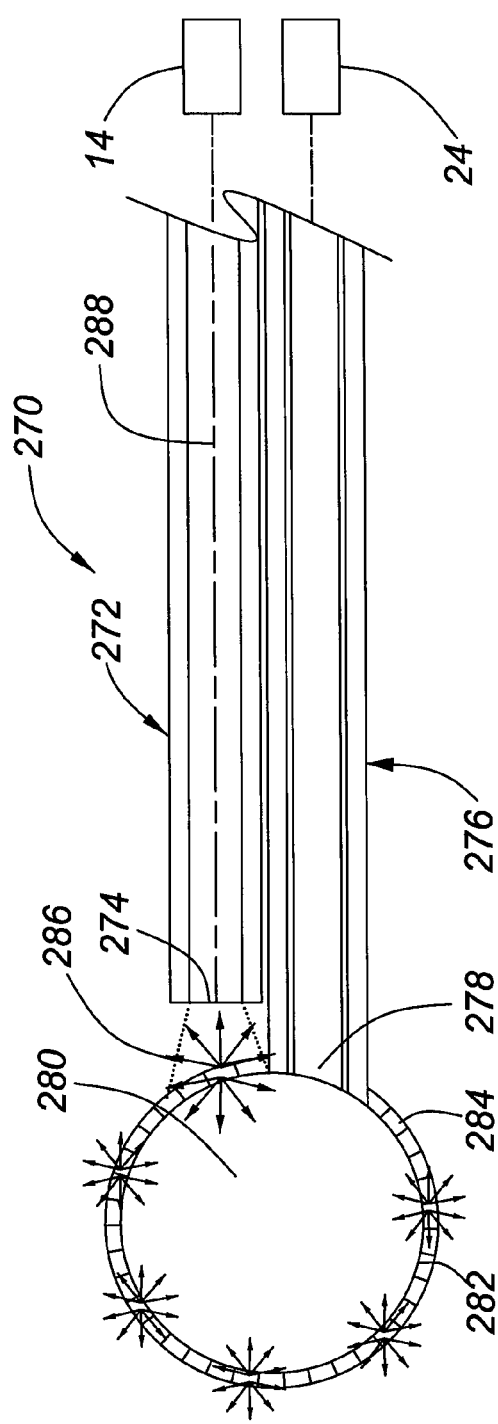
FIG. 17 is a diagrammatic side section view of another non-limiting embodiment of the invention.

According to another non-limiting embodiment of the invention, FIG. 17 illustrates a fiber optic probe 270 comprising an illuminating fiber 272 for guiding excitation light from a light source 14 to be launched from an end face 274 of the illuminating fiber 272. A second, receiving fiber 276 is arranged so that an end portion 278 of the receiving fiber protrudes past the end face 274 of the illuminating fiber 272. The receiving fiber 276 is a photonic crystal fiber. The illuminating fiber may also be a photonic crystal fiber.

At least a portion of the end 278 of the receiving fiber 276 is covered by a lens 280, similar to the lens 232 described previously with respect to FIGS. 13, 14 and 15. As such, at least a portion of an outer surface 282 of the lens 280 is covered by a film 284 which is similar to the films described previously. The lens 280 is preferably formed or attached in such a way that it extends towards the end face 274 of the illuminating optical fiber 272, as shown, to optimize illumination of the film 284 by the illuminating optical fiber 272.

As shown in FIG. 17, the illuminating fiber 272 and the receiving fiber 276 are in side-by-side parallel relation. The launching cone 286 of the illuminating fiber 272 will be generally symmetric about the optical axis 288 of the illuminating fiber 272.

Figure 18:
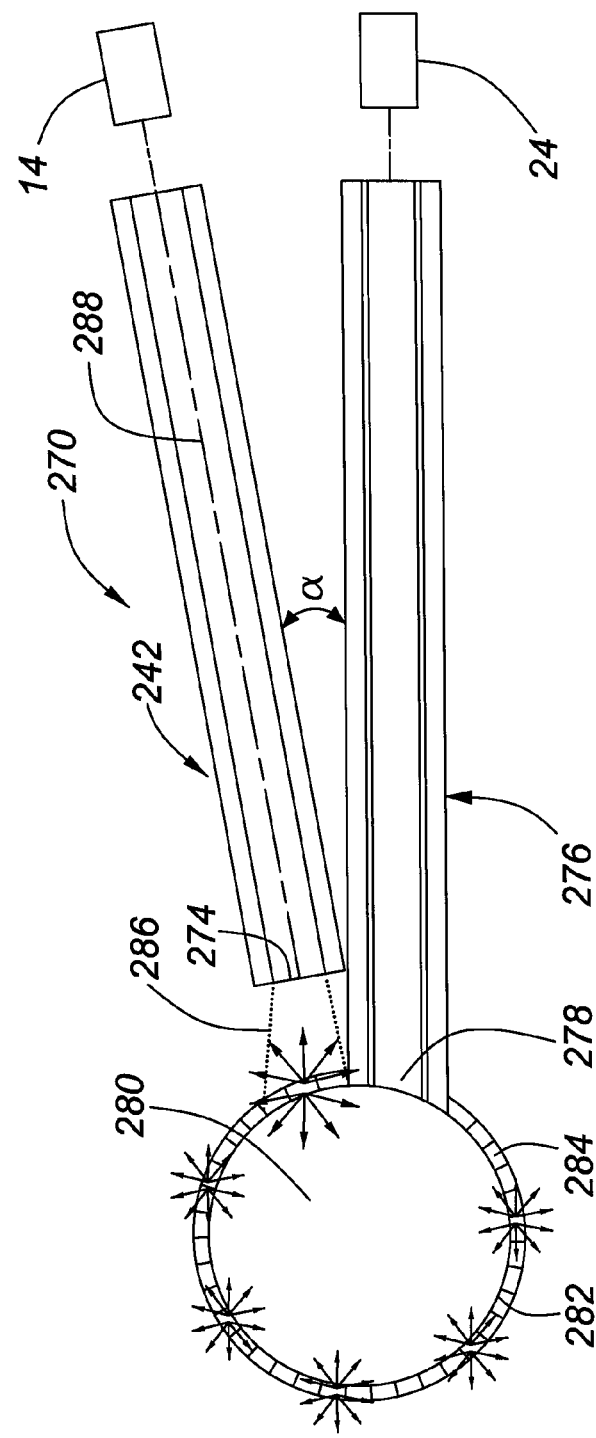
FIG. 18 is an alternative arrangement of the embodiment of FIG. 17.

Alternatively, as shown in FIG. 18, the illuminating fiber 272 may be disposed at a non-parallel angle α from the receiving fiber 276 to 'bend' or direct the launching cone 286 of the illuminating fiber 272 towards the film 284. By directing the launching cone 286 of the illuminating fiber 272 towards the film 284, the intensity of excitation light impinging upon the film 284 will be increased and the amount of light emitted by the film 284 and coupled into the receiving fiber 276 will increase. This angle α can range anywhere from about 0° to about 90°.

Figure 19:
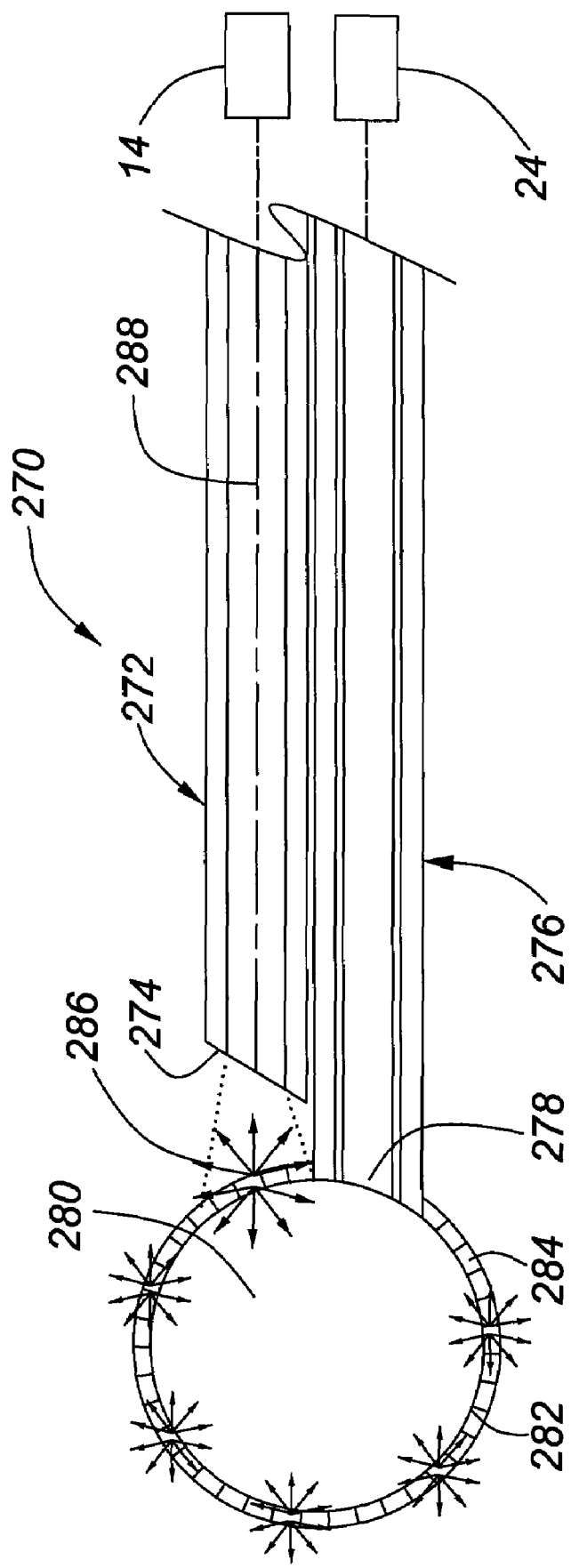
FIG. 19 is another alternative arrangement of the embodiment of FIG. 17.

Alternatively, as shown in FIG. 19, the end face 274 of the illuminating optical fiber 272 can be cut or polished at an angle to 'bend' or direct the launching cone 286 of the illuminating fiber 272 towards the film 284. As explained previously, by directing the launching cone 286 of the illuminating fiber 272 towards the film 284, the intensity of excitation light impinging upon the film 284 will be increased and the amount of light emitted by the film 284 and coupled into the receiving fiber 276 will increase.

Various fixtures may be implemented to hold the fiber(s) of any of the above described embodiments. Such fixtures are greatly simplified in the non-limiting embodiments described previously in which the film is applied directly to the fiber as the film itself does not need to be separately supported.

It should also be understood that, while in the above description of various embodiments of the invention, there is a single receiving fiber and a single illuminating fiber, embodiments of the invention may comprise multiple receiving fibers and/or multiple illuminating fibers. For example, a ring of receiving fibers may be provided around a single illuminating fiber.

It should be understood that a glass segment may be employed in example embodiments described herein having standard fibers by attaching a glass rod to the end of the receiving fiber via a gluing process, fusing process or any other suitable process. Such a glass segment would improve the light collection efficiency of the fiber in accordance with the principles described herein with reference to photonic crystal fiber.

We also refer to the following papers:
i) Jianjun Ma and Wojtek J. Bock, "*Modeling of photonic crystal fiber with air holes sealed at the fiber end and its application to fluorescent light collection efficiency enhancement*", Opt. Express 13, 2385-2393 (2005)
ii) Jianjun Ma et al., "*Towards optimum sample-probe-spectrometer system design by adjusting receiving fiber end face position and probe-membrane sample separation*", Opt. Express 13, 9492-9501 (2005)
iii) J. Ma et al., "*Investigation of large-core photonic crystal fiber sensor for enhancement of fluorescent light collection of polymer membrane*", Photonic Applications in Devices and Communication Systems, Proc. Of SPIE Vol. 5970, 597006 (2005)

While the invention has been described in detail in the foregoing specification, it will be understood by those skilled in the art that variations and departures may be made to particular aspects described therein without departing from the full scope of the invention. The full scope of the invention is intended to be derived from the patent specification as a whole including the claims. The invention is intended to include all reasonable equivalents of the various elements described herein, including equivalents that would be evident to skilled artisans at the time this application was made and also equivalents that become evident over time. It will be understood that advances in the technology and the state of the art in relation to this invention will make possible certain substitutions that will become evident over time, even if at the time of this application such equivalents and substitutions may not have been apparent.

We claim:

1. A fiber optic probe for detecting the presence or absence of one or more substances within a medium, said fiber optic probe comprising:
   at least one illuminating optical fiber for guiding excitation light from a light source to be launched from an end face of said at least one illuminating optical fiber;
   at least one film for emitting film-emitted light when illuminated by said excitation light, said film-emitted light having a central wavelength that is different than a central wavelength of said excitation light; and at least one receiving optical fiber for receiving and guiding said film-emitted light, said at least one receiving optical fiber being a photonic crystal fiber, an end portion of said at least one receiving optical fiber being a solid segment of glass.

wherein said end portion of said at least one receiving optical fiber is tapered.

2. A fiber optic probe according to claim 1, wherein the end portion of the at least one receiving optical fiber is proximate to the end portion of the at lease one illuminating optical fiber.

3. A fiber optic probe according to claim 1, wherein a longitudinal axis of the at least one illuminating optical fiber is oriented substantially parallel to a longitudinal axis of the at least one receiving optical fiber.

4. A fiber optic probe according to claim 1, wherein a longitudinal axis of the at least one illuminating optical fiber is oriented at an angle relative to a longitudinal axis of the at least one receiving optical fiber.

5. A fiber optic probe according to claim 1, wherein the end portion of the at least one receiving optical fiber protrudes beyond the end face of the at least one illuminating optical fiber.

6. A fiber optic probe according to claim 1, wherein the end face of the at least one illuminating optical fiber is angled relative to a longitudinal axis thereof.

7. A fiber optic probe according to claim 1, wherein the at least one illuminating optical fiber is integral with the at least one receiving optical fiber.

8. A fiber optic probe according to claim 1, wherein the film emits the film-emitted light by fluorescence.

9. A fiber optic probe according to claim 1, further comprising a sensor for detecting light received by the at least one receiving optical fiber.

10. A fiber optic probe according to claim 1, wherein the end portion of the at least one receiving optical fiber is retracted relative to the end face of the at least one illuminating optical fiber and the film is separate from both the end portion and the end face.

11. A fiber optic probe for detecting the presence or absence of one or more substances within a medium, said fiber optic probe comprising:

at least one illuminating optical fiber for guiding excitation light from a light source to be launched from an end face of said at least one illuminating optical fiber;

at least one film for emitting film-emitted light when illuminated by said excitation light, said film-emitted light having a central wavelength that is different than a central wavelength of said excitation light; and at least one receiving optical fiber for receiving and guiding said film-emitted light, said at least one receiving optical fiber being a photonic crystal fiber, an end portion of said at least one receiving optical fiber being a solid segment of glass;

wherein said segment of glass comprises an end portion of said receiving fiber wherein a plurality of air holes therein have been fused together to form said solid segment.

12. A fiber optic probe according to claim 11, wherein the end portion of the at least one receiving optical fiber is proximate to the end portion of the at least one illuminating optical fiber.

13. A fiber optic probe according to claim 11, wherein a longitudinal axis of the at least one illuminating optical fiber is oriented substantially parallel to a longitudinal axis of the at least one receiving optical fiber.

14. A fiber optic probe according to claim 11, wherein a longitudinal axis of the at least one illuminating optical fiber is oriented at an angle relative to a longitudinal axis of the at least one receiving optical fiber.

15. A fiber optic probe according to claim 11, wherein the end portion of the at least one receiving optical fiber protrudes beyond the end face of the at least one illuminating optical fiber.

16. A fiber optic probe according to claim 11, wherein the end face of the at least one illuminating optical fiber is angled relative to a longitudinal axis thereof.

17. A fiber optic probe according to claim 11, wherein the at least one illuminating optical fiber is integral with the at least one receiving optical fiber.

18. A fiber optic probe according to claim 11, wherein the film emits the film-emitted light by fluorescence.

19. A fiber optic probe according to claim 11, further comprising a sensor for detecting light received by the at least one receiving optical fiber.

20. A fiber optic probe according to claim 11, wherein the end portion of the at least one receiving optical fiber is retracted relative to the end face of the at least one illuminating optical fiber and the film is separate from both the end portion and the end face.

* * * * *